United States Patent [19]
Becker et al.

[11] Patent Number: 5,728,893
[45] Date of Patent: Mar. 17, 1998

[54] PROCESS USING MULTISTAGED REACTORS

[75] Inventors: Michael Carl Becker, League City, Tex.; David Robert Bryant; Donald LeRoy Bunning, both of South Charleston, W. Va.; James Clair Nicholson, St. Albans; Ernst Billig, Huntington, both of W. Va.

[73] Assignee: Union Carbide Chemicals & Plastics Technology Corporation, Danbury, Conn.

[21] Appl. No.: 757,743

[22] Filed: Nov. 26, 1996

Related U.S. Application Data

[60] Provisional application Nos. 60/008,763, 60/008,289, 60/008,284 and 60/008,286, all filed Dec. 16, 1995.

[51] Int. Cl.$^6$ .................................................. C07C 45/50
[52] U.S. Cl. ........................................ 568/454; 568/451
[58] Field of Search .................................. 568/454, 451

[56] References Cited

U.S. PATENT DOCUMENTS

| | | |
|---|---|---|
| T896,030 | 3/1972 | Westermann et al. . |
| 1,338,698 | 5/1920 | Richardson . |
| 2,192,124 | 2/1940 | Brill et al. . |
| 2,582,899 | 1/1952 | Barnebey et al. . |
| 2,590,436 | 3/1952 | Luten, Jr. . |
| 2,757,202 | 7/1956 | Mertzweiller et al. . |
| 3,194,638 | 7/1965 | Neuville . |
| 3,222,141 | 12/1965 | Donaldson . |
| 3,266,872 | 8/1966 | Terao et al. . |
| 3,271,458 | 9/1966 | Ellis et al. . |
| 3,868,422 | 2/1975 | Hart et al. . |
| 3,909,207 | 9/1975 | Bir . |
| 3,950,138 | 4/1976 | Wolf et al. . |
| 4,374,093 | 2/1983 | Rollmann et al. . |
| 4,483,624 | 11/1984 | Bacon, Jr. et al. . |
| 4,996,029 | 2/1991 | Martin et al. . |
| 5,073,311 | 12/1991 | Nojima et al. . |
| 5,098,669 | 3/1992 | Kawanami et al. . |
| 5,410,091 | 4/1995 | Nall . |

FOREIGN PATENT DOCUMENTS 0423769  4/1991  European Pat. Off. .

Primary Examiner—Gary Geist
Assistant Examiner—Sreeni Padmanabhan
Attorney, Agent, or Firm—G. L. Coon

[57] ABSTRACT

This invention relates to a process for producing one or more products in a staged reactor having more than one reactive stage which process comprises reacting in said staged reactor one or more reactants with carbon monoxide in the presence of a metal-organophosphorus ligand complex catalyst and optionally free organophosphorus ligand to produce said one or more products, wherein said metal-organophosphorus ligand complex catalyst does not undergo substantial deactivation in the presence of solely carbon monoxide and/or effects a change in normal product selectivity of less than 0.2 percent of normal product per 1 pound per square inch of carbon monoxide partial pressure and/or effects a change in reaction rate of less than 2 percent per 1 pound per square inch of carbon monoxide partial pressure.

14 Claims, No Drawings

PROCESS USING MULTISTAGED REACTORS

This application claims the benefit of provisional U.S. patent application Ser. Nos. 60/008763, 60/008289, 60/008284 and 60/008286, all filed Dec. 6, 1995, and all of which are incorporated herein by reference.

BRIEF SUMMARY OF THE INVENTION

TECHNICAL FIELD

This invention relates to certain metal-organophosphorus ligand complex catalyzed processes, e.g., carbonylation and hydroformylation, that can be conducted in a multistaged reactor.

BACKGROUND OF THE INVENTION

Conventional continuously stirred tank reactor (CSTR) vessels employed in chemical processes provide only one theoretical reactive stage per vessel. Where the objective is to push a reaction to completion and the extent of conversion is not limited by equilibrium, it is advantageous to have a number of reactive stages in series. Otherwise the valued reactant must be recovered and recycled through the reaction system. Normally, a reaction to completion in a single pass through the system is accomplished by putting several conventional continuously stirred tank reactors in series. It would be desirable to conduct processes in reactors designed with multiple stages that create more than one theoretical reactive stage per vessel.

A disadvantage of conducting processes employing carbon monoxide in a multistaged reactor is that normal product selectivity using rhodium-triphenylphosphine complex catalysts shows a significant response to changing carbon monoxide partial pressure and/or the total reaction rate shows a significant response to changing carbon monoxide partial pressure. Also, rhodium-triphenylphosphine complex catalysts deactivate in the presence of carbon monoxide and hydrogen alone (in the absence of olefin). A successful method for conducting processes employing carbon monoxide in a multistaged reactor would be desirable in the art.

DISCLOSURE OF THE INVENTION

It has been discovered that certain metal-organophosphorus ligand complex catalyzed processes, e.g., carbonylation and hydroformylation, in which the metal-organophosphorus ligand complex catalyst does not exhibit substantial deactivation in the presence of solely carbon monoxide or solely carbon monoxide and hydrogen and/or in which the normal product selectivity does not exhibit a significant response to changing carbon monoxide partial pressure and/or in which the reaction does not exhibit a significant response to changing carbon monoxide partial pressure, can be conducted in a multistaged reactor. Thus, this invention improves the economics of metal-organophosphorus ligand complex catalyzed processes which employ carbon monoxide by eliminating the need for separate multiple reactors and the higher capital costs associated therewith.

This invention relates in part to a process for producing one or more products in a staged reactor having more than one reactive stage which process comprises reacting in said staged reactor one or more reactants with carbon monoxide in the presence of a metal-organophosphorus ligand complex catalyst and optionally free organophosphorus ligand to produce said one or more products, wherein said metal-organophosphorus ligand complex catalyst does not undergo substantial deactivation in the presence of solely carbon monoxide and/or effects a change in normal product selectivity of less than 0.2 percent of normal product per 1 pound per square inch of carbon monoxide partial pressure.

This invention also relates in part to a hydroformylation process for producing one or more aldehydes in a staged reactor having more than one reactive stage which process comprises reacting in said staged reactor one or more olefinic unsaturated compounds with carbon monoxide and hydrogen in the presence of a metal-organophosphorus ligand complex catalyst and optionally free organophosphorus ligand to produce said one or more aldehydes, wherein said metal-organophosphorus ligand complex catalyst does not undergo substantial deactivation in the presence of solely carbon monoxide and hydrogen and/or effects a change in normal aldehyde selectivity of less than 0.2 percent of normal aldehyde per 1 pound per square inch of carbon monoxide partial pressure.

This invention further relates in part to a process for producing one or more products in a staged reactor having more than one reactive stage which process comprises reacting in said staged reactor one or more reactants with carbon monoxide in the presence of a metal-organophosphorus ligand complex catalyst and optionally free organophosphorus ligand to produce said one or more products, wherein said metal-organophosphorus ligand complex catalyst does not undergo substantial deactivation in the presence of solely carbon monoxide and/or effects a change in normal product selectivity of less than 0.2 percent of normal product per 1 pound per square inch of carbon monoxide partial pressure and/or effects a change in reaction rate of less than 2 percent per 1 pound per square inch of carbon monoxide partial pressure.

This invention yet further relates in part to a hydroformylation process for producing one or more aldehydes in a staged reactor having more than one reactive stage which process comprises reacting in said staged reactor one or more olefinic unsaturated compounds with carbon monoxide and hydrogen in the presence of a metal-organophosphorus ligand complex catalyst and optionally free organophosphorus ligand to produce said one or more aldehydes, wherein said metal-organophosphorus ligand complex catalyst does not undergo substantial deactivation in the presence of solely carbon monoxide and hydrogen and/or effects a change in normal aldehyde selectivity of less than 0.2 percent of normal aldehyde per 1 pound per square inch of carbon monoxide partial pressure and/or effects a change in reaction rate of less than 2 percent per 1 pound per square inch of carbon monoxide partial pressure.

DETAILED DESCRIPTION

In addition to the advantages of high raw material conversion and/or reduced total reactor volume resulting from employing multistaged reactors in the processes of this invention, additional advantages of this invention include, for example, reduced consumption of the valuable metal-organophosphorus ligand complex catalyst due to lower total reactor volume, reduced formation of heavy byproducts due to lower total reactor volume, elimination of expensive and complicated equipment for olefin recovery and recycle equipment due to high conversion, and ability to use less pure feedstocks directly and efficiently.

The multistaged reactor useful in this invention preferably comprises an elongated reactor vessel positioned substantially vertically, containing at least one, and preferably two or more, ingress means, and at least one, preferably two or more, egress means. The ingress means may be placed in the bottom portion of the reactor vessel and the egress means in the top portion of the reactor vessel. The reactants are continuously introduced into the ingress means and the products and unreacted reactants are continuously withdrawn from the egress means. A mixing means, e.g., a stirrer, with a plurality of blades is placed inside the reactor and it extends substantially through the entire length of the reactor. In addition, the inside wall surface of the reactor is preferably equipped with a number of baffle means fitting in-between the blades of the stirrer. The reactor vessel may also be equipped with a heat removal means, e.g., a heat exchanger or internal cooling coils, to maintain the reactants at the desired reaction temperature.

The reactor may be of a generally elongated shape, e.g., a tube, preferably cylindrical in shape, whose overall volume depends on the desired throughput and on the product being synthesized in the reactor. The ratio of the length of the reactor to its diameter is not narrowly critical and is determined by the number of reaction zones that it contains.

The reactants may be introduced into the reactor vessel through entrance means in the lower portion and upper portion of the reactor vessel. For hydroformylation, illustrative reactants entrance means in the lower portion of the reactor vessel include: (i) a first reactants entrance means for continuously conveying one or more catalysts and optionally one or more olefinic compounds into the reactor means; and (ii) a second reactants entrance means for continuously conveying a source of hydrogen and carbon monoxide and optionally one or more olefinic compounds into the reactor means. The first reactants entrance means may be positioned on the same or opposite side of the reactor means as the second reactants entrance means. A third reactants entrance means for continuously conveying one or more olefinic compounds into the reactor means can preferably be used in the event that the one or more olefinic compounds are not conveyed by the first or second reactants entrance means. The reactants entrance means in the upper portion of the reactor means preferably comprise one or more reactants entrance means for continuously conveying one or more olefinic compounds, one or more catalysts and/or a source of hydrogen and carbon monoxide into the reactor means, preferably continuously conveying a source of hydrogen and carbon monoxide into said reactor means.

In an embodiment, the reactor is positioned substantially vertically. The term substantially vertically as used herein designates such positioning of the reactor which enables gases to be advanced upwardly. Thus, the reactor may be positioned at 60° to 90° from the horizontal.

A stirring means, comprising an elongated rod, extending throughout the length of the reactor and having a plurality of blades, may be placed inside the reactor vessel in such a manner that it extends substantially through the entire length of the reactor, thereby insuring efficient and uniform mixing of the hydroformylation reactants. The blades may be disposed in any manner to effect proper mixing. The rod with the alternating blades is continuously rotated by conventional motor means, preferably placed outside the reactor vessel, during the course of the reaction.

In addition, the inner surface of the reactor vessel preferably contains a number of baffles generally horizontal or inclined at the similar angle as the blades of the stirrer and spaced at such intervals that they fit in-between the stirrer. The combination of the baffles and the rotating stirrer blades provides sufficient turbulence for the reactants to assure proper contacting for the reactions to take place.

The products and unreacted reactants can be recovered from the reactor vessel at the top of the reactor into a product collecting means or further transferred to a product separating means or a next reactor in series by means of a conduit optionally equipped with a valve means. A purpose of the valve is to allow one to isolate the reactor vessel from the product collecting means or product separating means or next reactor in series. The product exit means in the upper portion of the reactor means preferably comprise: (i) a first product exit means for continuously removing product and catalyst and unreacted reactants from the reactor means; and (ii) a second product exit means for continuously removing product and unreacted reactants from the reactor means.

The composite parts of the multistaged reactor can be constructed from any commonly used construction materials which are inert to the reactants and products. Thus, the reactor vessel can be made of high grade stainless steel, with inside walls of the reactor being polished to prevent deposits thereon. The stirrer of the reactor may also be made of stainless steel with blades welded or bolted thereto, or the blades and the stirrer may be made from a unitary block of material, e.g., cast from metal. See, for example, U.S. Pat. Nos. 3,194,638, 3,222,141, 3,266,872, 3,950,138, 4,374,093, 4,483,624, 5,073,311, 5,098,669, T 896,030, 1,338,698, 2,192,124, 2,582,899, 2,590,436, 3,909,207, and 4,996,029, the disclosures of which are incorporated herein by reference. See also, for example, Fasano, Julian B., W. Roy Penney, and Bang Cheng Xu, "Design and Scaleup of Compartmented, Staged Process Equipment with Emphasis on Interstage Backmixing," Presentation given at the 14th Bi-Annual Engineering Foundation Mixing Conference at Santa Barbara, Calif., Jun. 20 to 24, 1993; Prengle, H. William, Jr., and Narses Barona, "Make Petrochemicals by Liquid Phase Oxidation: Part 2: Kinetics, Mass Transfer and Reactor Design," Hydrocarbon Processing, November 1970, pp. 159–175; and Oldshue, J. Y., and J. H. Rushton, "Continuous Extraction in a Multistage Mixer Column", Chemical Engineering Progress, Vol. 48, June 1952, pp.297–306; the disclosures of which are incorporated herein by reference.

In a preferred embodiment, the multistaged reactor useful in this invention comprises a vessel adapted to contain a carbonylation or hydroformylation reaction. The interior of the vessel may be divided into a number of chambers of the same or different sizes by means of generally horizontal baffles extending inwardly from the interior wall of the vessel. Each baffle has a hole generally in its central portion and each hole is aligned with each other hole. A common shaft extends generally vertically through the holes in the horizontal baffles. A plurality of impellers are rotatably mounted on the drive shaft such that an impeller is disposed above the hole of each baffle.

In a preferred embodiment, the multistaged reactor comprises a substantially vertically-oriented reactor means; a stirring means inside said reactor means, said stirring means being operatively associated with said reactor means and comprising an elongated rod means having a plurality of blades disposed about said rod means, said stirring means extending substantially throughout the entire length of said reactor means; at least two reactants entrance means in the lower portion of said reactor means for continuously conveying one or more olefinic compounds, one or more metal-organophosphorus ligand complex catalysts and a source of hydrogen and carbon monoxide into said reactor means; optionally at least one reactants entrance means in the upper portion of said reactor means for continuously conveying one or more olefinic compounds, one or more metal-organophosphorus ligand complex catalysts and/or a source of hydrogen and carbon monoxide into said reactor means; at least one product exit means in the upper portion of said reactor means for continuously removing product, metal-organophosphorus ligand complex catalyst and unreacted reactants from said reactor means; and at least one baffle means on the inside surface of said reactor means, said baffle means being spaced in such a manner that said baffle means are interspaced in-between said stirring means.

The multistaged reactor preferably further comprises heat removal means comprising external loop or internal coils. The reactants entrance means in the lower portion of said reactor means preferably comprise: (i) a first reactants entrance means for continuously conveying one or more metal-organophosphorus ligand complex catalysts and optionally one or more olefinic compounds into said reactor means; and (ii) a second reactants entrance means for continuously conveying a source of hydrogen and carbon monoxide and optionally one or more olefinic compounds into said reactor means. A third reactants entrance means for continuously conveying one or more olefinic compounds into said reactor means can preferably be used in the event that the one or more olefinic compounds are not conveyed by the first or second reactants entrance means. The reactants entrance means in the upper portion of said reactor means preferably comprise one or more reactants entrance means for continuously conveying a source of hydrogen and carbon monoxide into said reactor means. The product exit means in the upper portion of said reactor means preferably comprise: (i) a first product exit means for continuously removing product and metal-organophosphorus ligand complex catalyst and unreacted reactants from said reactor means; and (ii) a second product exit means for continuously removing product and unreacted reactants from said reactor means.

In another embodiment, the multistaged reactors useful in this invention comprise a substantially vertically-oriented vessel; a plurality of generally horizontal baffles disposed within said vessel and dividing the interior of said vessel into a plurality of chambers, each said baffle being formed with a central hole and being mounted on the inner wall of said vessel; at least two inlet means for feeding one or more olefinic compounds, one or more metal-organophosphorus ligand complex catalysts and a source of hydrogen and carbon monoxide into one or more lower chambers; optionally at least one inlet means for feeding one or more olefinic compounds, one or more metal-organophosphorus ligand complex catalysts and/or a source of hydrogen and carbon monoxide into one or more upper chambers; at least one outlet means for removing hydroformylation products, metal-organophosphorus ligand complex catalysts and unreacted reactants from one or more upper chambers; a rotatable generally vertical drive shaft centrally positioned to rotate in said vessel and extending generally concentrically through each said hole in each said baffle; and a plurality of impellers each mounted for rotation on said shaft and generally positioned above or below each said hole of said horizontal baffles, said impellers being of a size relative to said holes to sufficiently provide mixing of said hydroformylation reactants, metal-organophosphorus ligand complex catalysts and products as they move from a lower chamber upward to an adjacent chamber whereby said hydroformylation reactants, metal-organophosphorus ligand complex catalysts and products are caused to be mixed within each chamber.

The multistaged reactor preferably further comprises heat removal means comprising external loop or internal coils.

The inlet means in one or more lower chambers of said vessel preferably comprise: (i) a first inlet means for feeding one or more metal-organophosphorus ligand complex catalysts and optionally one or more olefinic compounds into said vessel; and (ii) a second inlet means for feeding a source of hydrogen and carbon monoxide and optionally one or more olefinic compounds into said vessel. A third inlet means for feeding one or more olefinic compounds into said vessel can preferably be used in the event that the one or more olefinic compounds are not fed by the first or second inlet means. The inlet means in one or more upper chambers of said vessel preferably comprise one or more inlet means for feeding a source of hydrogen and/or carbon monoxide into said vessel. The outlet means in one or more upper chambers of said vessel preferably comprise: (i) a first outlet means for removing product and metal-organophosphorus ligand complex catalyst and unreacted reactants from said vessel; and (ii) a second outlet means for removing product and unreacted reactants from said vessel.

In yet another embodiment, the multistaged reactors useful in this invention comprise a vertical cylindrical vessel with a plurality of spaced stationary horizontal imperforate baffles dividing said vessel into compartments, said baffles having central apertures therein for communication between said compartments; an upstanding flange disposed around the circumference of the central aperture of each compartment; a shaft rotatably mounted axially of said vessel and extending through said compartments and an agitating means for the shaft; a means for admitting carbon monoxide, hydrogen, one or more metal-organophosphorus ligand complex catalysts and one or more olefinic compounds into the lower-most compartment; and a means for withdrawing product aldehyde, metal-organophosphorus ligand complex catalyst and unreacted reactants from the upper-most compartment.

In still another embodiment, the multistaged reactors useful in this invention comprise a reactor means sectioned into a plurality of compartments by baffle plates; cooling means to adjust the temperature of said reactor means; means for admitting carbon monoxide, hydrogen, one or more metal-organophosphorus ligand complex catalysts and one or more olefinic compounds into the lower-most compartment; and means for withdrawing product aldehyde, metal-organophosphorus ligand complex catalyst and unreacted reactants from the upper-most compartment.

In another embodiment, the multistaged reactors useful in this invention comprise a vessel with an elongated generally cylindrical chamber therein; an agitator shaft extending coaxially through the chamber, the shaft extending outside the chamber and being provided with means for driving the same; a plurality of transverse partitions in the chamber open at their centers around the agitating shaft dividing the chamber into a lineal series of compartments; an agitator for providing mixing in each compartment; vertical baffles in each compartment projecting radially toward the center to prevent swirling of fluids being agitated, designed to produce in each compartment upon rotation of the agitator a cyclical flow of fluid and gas from the periphery of the agitator to the peripheral wall of the chamber, thence lengthwise of the chamber in each direction along the walls of the compartment, and thence radially inwardly adjacent said partitions toward the shaft; a means for admitting carbon monoxide, hydrogen, one or more metal-organophosphorus ligand complex catalysts and one or more olefinic compounds into the lower-most compartment; and a means of withdrawing product aldehyde, metal-organophosphorus ligand complex catalyst and unconverted reactants from the upper-most compartment.

In yet another embodiment, the multistaged reactors useful in this invention comprise a reactor means with a plurality of generally horizontal baffles disposed within said reactor means and dividing the interior of said reactor means into a plurality of chambers; each said baffle being formed with a central hole and being mounted on the inner wall of said reactor means so that the products, metal-organophosphorus ligand complex catalysts and reactants traveling upwardly in said reactor means must pass through the central hole in each baffle; a rotatable generally vertical drive shaft centrally positioned to rotate in said reactor means and extending generally concentrically through each said hole in each said baffle; a plurality of impellers each mounted for rotation on said drive shaft; inlet means for feeding carbon monoxide, hydrogen, one or more metal-organophosphorus ligand complex catalysts and one or more olefinic compounds into the bottom-most compartment of the reactor means; outlet means for removing product aldehyde, metal-organophosphorus ligand complex catalyst and unreacted reactants from the upper-most compartment; and optionally wherein the concentration of carbon monoxide in reactor means blowoff is greater than about 8 mole percent.

The reactors useful in this invention may be designed with internal, physical barriers that create more than one theoretical reactive stage per vessel. In effect, it is like having a number of reactors inside a single continuous stirred tank reactor (CSTR) vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators. This invention is not intended to be limited in any manner by the permissible multistaged reactors.

As indicated above, it has been discovered that certain metal-organophosphorus ligand complex catalyzed processes in which the metal-organophosphorus ligand complex catalyst does not exhibit substantial deactivation in the presence of solely carbon monoxide or solely carbon monoxide and hydrogen and/or in which the normal product selectivity does not exhibit a significant response to changing carbon monoxide partial pressure and/or in which the reaction does not exhibit a significant response to changing carbon monoxide partial pressure, can be conducted in a multistaged reactor.

The metal-organophosphorus ligand complex catalysts useful in this invention do not undergo substantial deactivation in the presence of solely carbon monoxide or solely carbon monoxide and hydrogen. In particular, metal-ligand complex catalysts employing a metal, e.g., rhodium, and organophosphite or certain organophosphine ligands useful in this invention do not deactivate when exposed to very high (greater than 60 psi) synthesis gas partial pressures alone, thereby providing operational flexibility for the reactors and the internal stages. In contrast, metal-ligand complex catalysts employing triphenylphosphine ligand deactivate at high carbon monoxide partial pressures in the absence of olefin. The low carbon monoxide partial pressure required, for example, by rhodium-triphenylphosphine ligand complex catalyst in propylene or butene hydroformylation processes, makes such a system more sensitive to changes in carbon monoxide partial pressure, thus making it difficult to control in a reactor with internal staging.

Also, the metal-organophosphorus ligand complex catalyzed processes of this invention give a normal product selectivity that does not show a significant response to carbon monoxide partial pressure. In particular, the metal-ligand complex catalysts employing a metal, e.g., rhodium, and organophosphite or certain organophosphine ligand useful in this invention effect a change in normal product, e.g., aldehyde, selectivity of less than 0.2 percent of normal product, e.g., aldehyde, per 1 pound per square inch of carbon monoxide partial pressure. In contrast, the normal product selectivity shows a significant response to changing carbon monoxide partial pressure in conventional processes employing metal-triphenylphosphine ligand complex catalysts. For purposes of this invention, it is to be understood that a change in normal product, e.g., aldehyde, includes an all normal product (no branched product) such as propionaldehyde resulting from the hydroformylation of ethylene.

Further, the metal-organophosphorus ligand complex catalyzed processes of this invention give a reaction rate that does not show a significant response to carbon monoxide partial pressure. In particular, the metal-ligand complex catalysts employing a metal, e.g., rhodium, and organophosphite or certain organophosphine ligand useful in this invention effect a change in reaction rate of less than 2 percent per 1 pound per square inch change of carbon monoxide partial pressure. In contrast, in conventional processes the normal reaction rate shows a significant response to changing carbon monoxide partial pressure employing metal-triphenylphosphine ligand complex catalysts. For example, in a rhodium/triphenylphosphine catalyst system for propylene hydroformylation, the reaction rate changes by about 5 percent or more for a 1 pound per square inch change in carbon monoxide partial pressure at typical conditions for commercial application. This large change in reaction rate for a small fluctuation in carbon monoxide makes such a system more sensitive to changes in carbon monoxide partial pressure, thus making it difficult to control in a reactor with internal staging. For purposes of this invention, a change in reaction rate refers to the reaction rate of the main products and does not include byproducts. Also, for purposes of this invention, a change in reaction rate is contemplated to mean the absolute value of the reaction rate change.

The multistaged reactors useful in this invention are highly desirable for conducting processes employing carbon monoxide, preferably carbonylation and hydroformylation reactions. The reactors of this invention have more than one theoretical stage. Internal barriers provide the staging. Gas and liquid flow are co-current or counter-current. The internal staging is being done at the same time a gas/liquid reaction is taking place. Heat of reaction can be removed both by an external heat exchanger and by internal cooling coils because of the changing heat loads in the different reactor compartments. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

This invention is useful for improving the economics of processes which employ carbon monoxide. Typically, one or multiple CSTR reactors are used in series to increase raw material, e.g., olefin, conversion. While multiple reactors increase conversion, the proliferation of equipment to achieve this efficiency results in a higher capital cost for the facilities. This invention addresses that cost by providing for multiple reaction stages in a single vessel, dramatically reducing installed cost of the facilities.

The multistaged reactors useful in this invention can be used in any process with a homogeneous catalyst where CSTRs ordinarily would be used. The invention in part involves conducting a reaction in a vertical cylindrical vessel with a plurality of reaction zones. The reaction zones are characterized by the fact that they preferably are essentially back-mixed, and the concentration of carbon monoxide in the blowoff gas of the last reaction zone may preferably be greater than 8 mole percent.

This invention is distinctive in applying the baffled reactor concept to reaction systems using organophosphites and certain organophosphines as catalyst ligands. This invention provides for lower capital costs for a reaction process which achieves a high efficiency. This invention also provides for a simplified control scheme for the reaction part of a process. This invention applies to any process, e.g., hydroformylation, with organophosphite and certain organophosphine ligands, with catalysts in a liquid phase, and with any olefin or olefins. It is mainly useful under reaction conditions where normal product selectivity is a relatively insensitive function of hydrogen or carbon monoxide partial pressure. For organophosphite ligands and certain organophosphine ligands, it is primarily useful when the carbon monoxide partial pressure is higher that about 20 psi. In an embodiment of this invention, the mole percent of carbon monoxide in the gas blowoff from the last zone may be greater than about 8 percent, e.g., when the total reactor pressure is 300 psia, then the total carbon monoxide partial pressure will be 24 psia.

Operating in the region where the reaction rate changes from positive order in carbon monoxide to negative order in carbon monoxide is less desirable because of increased operating complexities. In a preferred embodiment, sufficient olefin is present to prevent and/or lessen intrinsic deactivation of the metal-organophosphorus ligand complex catalyst so that activity decline, if any, is less than about 50 percent deactivation of the metal-organophosphorus ligand complex catalyst (per 30 days of continuous operation with reference to the highest activation level of said metal-organophosphorus ligand complex catalyst).

Reaction zones should provide good gas/liquid mixing, good liquid/liquid mixing, and in some cases provide required heat transfer. Length/diameter per stage may be from about 0.5 to about 2.0 or greater; about 1:1 is preferred. The number of reaction zones should be about 2–30 or greater, preferably about 2–20, more preferably about 2–10. Gas and liquid flow is co-current or counter-current and upflow or down flow from zone to zone. Heat of reaction can be removed by external loop and/or internal coils. The external heat exchangers can remove more heat. Mixing within stages can be by mechanical agitator or by circulating pump or other methods.

Reaction zones can be physically separated by baffle plates with passages from one stage to next where the passages are such that gas and liquid backflow is minimized. Reaction zones can also be separated by properly designed mixing patterns which create regions of varying concentrations but still allow for bulk gas and liquid flow from zone to zone. Physical passages from one stage to the next need only be located so that backflow between stages is minimized and mixing within stages is achieved; one preferred way is, when mechanical agitation is used, to have the complete flow come through a hole under the agitator.

Reactant feed location may vary in the multistaged reactor. For hydroformylation, olefin feed is generally not in last stage; preferably in the first two stages; most preferably in the first stage only. Synthesis gas (carbon monoxide and hydrogen) feed can be in all stages. Feeds are introduced near the bottom of each stage. Olefin concentration may drop from zone to zone co-current with the liquid flow. Hydroformylation product mixture is removed from the final zone.

General Processes

The processes of this invention which use multistaged reactors may be asymmetric or non-asymmetric, the preferred processes being non-asymmetric, and may be conducted in any continuous or semi-continuous fashion and may involve any catalyst liquid and/or gas recycle operation desired. The particular processes for producing products from one or more reactants, as well as certain of the reaction conditions and ingredients of the processes are not critical features of this invention. The processing techniques of this invention may correspond to any of the known processing techniques heretofore employed in conventional processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion.

Illustrative processes include, for example, hydroformylation, hydroacylation (intramolecular and intermolecular), hydroamidation, hydroesterification, carbonylation and the like. Preferred processes involve the reaction of organic compounds with carbon monoxide, or with carbon monoxide and a third reactant, e.g., hydrogen, in the presence of a catalytic amount of a metal-organophosphorus ligand complex catalyst. The most preferred processes include hydroformylation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organophosphorus ligand complex catalyst described herein. Alternatively, hydroxyaldehydes can be prepared by reacting an epoxide, carbon monoxide and hydrogen under hydroformylation conditions in the presence of a metal-organophosphorus ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be convened to cyclic ketones under hydroacylation conditions in the presence of a metal-organophosphorus ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organophosphorus ligand complex catalyst described herein.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organophosphorus ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organophosphorus ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organophosphorus ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, intermolecular hydroacylation, hydroamidation, hydroesterification), epoxides (hydroformylation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-organophosphorus ligand complex catalysts employable in the processes encompassed by this invention as well as methods for their preparation are well known in the art and include those disclosed in the below mentioned patents, provided said metal-organophosphorus ligand complex catalysts do not undergo substantial deactivation in the presence of solely carbon monoxide and/or effect a change in normal product selectivity of less than 0.2 percent of normal product per 1 pound per square inch of carbon monoxide partial pressure. The term substantial deactivation as used herein designates greater than 50 percent deactivation of the metal-organophosphorus ligand complex catalyst (per 30 days of continuous operation with reference to the highest activation level of said metal-organophosphorus ligand complex catalyst). In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and RP(O)(OH)O (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2$=$CHCH_2$, $CH_3CH$=$CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred.

Among the organophosphines that may serve as the ligand of the metal-organophosphine complex catalyst and/or free organophosphine ligand of the reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may be substituted if desired, with any suitable substituent that does not unduly adversely affect the desired result of the hydroformylation reaction. The organophosphine ligands employable in the reactions and/or methods for their preparation are known in the art.

Illustrative triorganophosphine ligands may be represented by the formula:

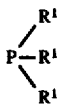

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radon the aryl radicals include, for example, alkyl radicals, alkoxy radicals, silyl radicals such as —Si(R$^2$)$_3$; amino radicals such as —N(R$^2$)$_2$; acyl radicals such as —C(O)R$^2$; carboxy radicals such as —C(O)OR$^2$; acyloxy radicals such as —OC(O)R$^2$; amido radicals such as —C(O)N(R$^2$)$_2$ and —N(R$^2$)C(O)R$^2$; sulfonyl radicals such as —SO$_2$R$^2$; ether radicals such as —OR$^2$; sulfinyl radicals such as —SOR$^2$; sulfenyl radicals such as —SR$^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N(R$^2$)$_2$, each $R^2$ taken together can also represent a divalent bridging group that forms a heterocyclic radical with the nitrogen atom and in amido substituents such as C(O)N(R$^2$)$_2$ and —N(R$^2$)C(O)R$^2$ each —R$^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, for example, triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphosphines, for example, of (tri-m-sulfophenyl)phosphine and of(m-sulfophenyl) diphenyl-phosphine and the like.

More particularly, illustrative metal-organophosphine complex catalysts and illustrative free organophosphine ligands include, for example, those disclosed in U.S. Pat. Nos. 3,527,809; 4,148,830; 4,247,486; 4,283,562; 4,400, 548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

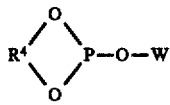

(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

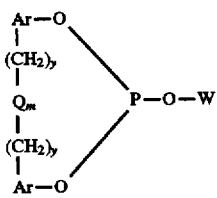

(IV)

wherein W is as defined above, each Ar is the same or different and represents a substituted or unsubstituted aryl radical, each y is the same or different and is a value of 0 or 1, Q represents a divalent bridging group selected from —C($R^5$)$_2$—, —O—, —S—, —$NR^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

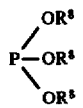

(V)

wherein each $R^8$ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for $R^1$ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

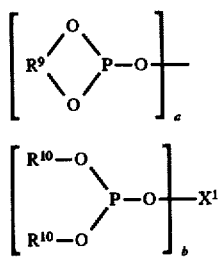

(VI)

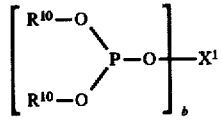

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-(CH$_2$),—$Q_m$—(CH$_2$),-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

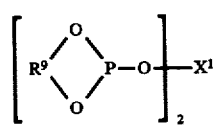

(VII)

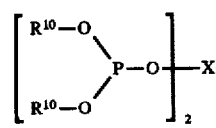

(VIII)

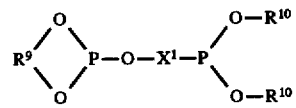

(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobis-phosphites are those of the following formulas (X) to (XII):

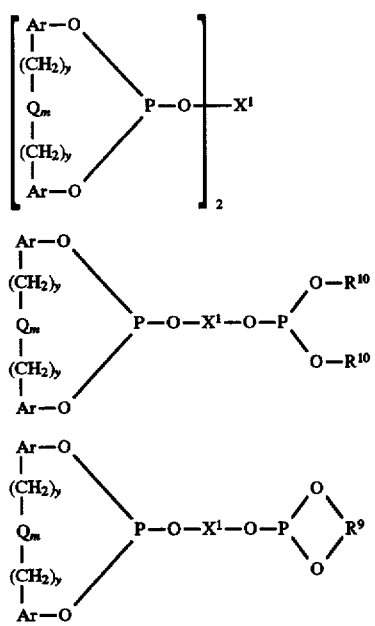

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —$Si(R^{12})_3$; amino radicals such as —$N(R^{12})_2$; phosphine radicals such as -aryl-$P(R^{12})_2$; acyl radicals such as —C(O) $R^{12}$; acyloxy radicals such as —$OC(O)R^{12}$; amido radicals such as —$CON(R^{12})_2$ and —$N(R^{12})COR^{12}$; sulfonyl radicals such as —$SO_2R^{12}$; alkoxy radicals such as —$OR^{12}$; sulfinyl radicals such as —$SOR^{12}$; sulfenyl radicals such as —$SR^{12}$; phosphonyl radicals such as —$P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —$N(R^{12})_2$ each $R^{12}$ taken together can also represent a divalent bridging group that forms a heterocyclic radical with the nitrogen atom, and in amido substituents such as —$C(O)N(R^{12})_2$ and —$N(R^{12})COR^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, — $OCH_2CH_2OCH_3$, —$(OCH_2CH_2)_2OCH_3$, —$(OCH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; sulfenyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of organophosphite ligands include the following:

2-t-butyl-4-methoxyphenyl(3,3'-di-t-butyl-5,5'-dimethoxy-1,1'-biphenyl-2,2'-diyl)phosphite having the formula:

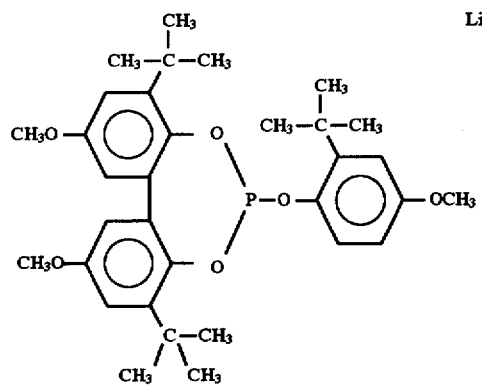

Ligand A methyl(3,3'-di-t-butyl-5,5'-dimethoxy-1,1'-biphenyl-2,2'-diyl)phosphite having the formula:

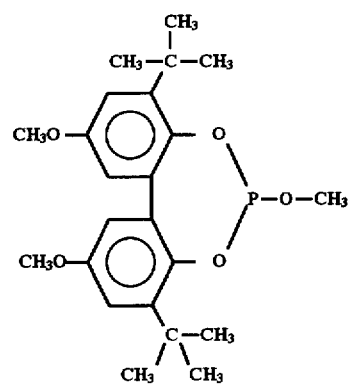

Ligand B 6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

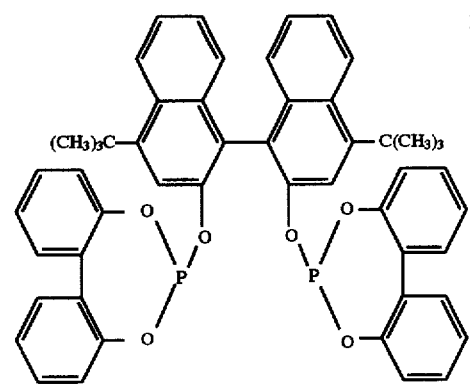

Ligand C 6,6'-[[3,3'-bis(1,1-dimethylethyl)-5,5'-dimethoxy-[1,1'-biphenyl]-2,2'-diyl]bis(oxy)]bis-dibenzo[d,f][1,3,2] dioxaphosphepin having the formula:

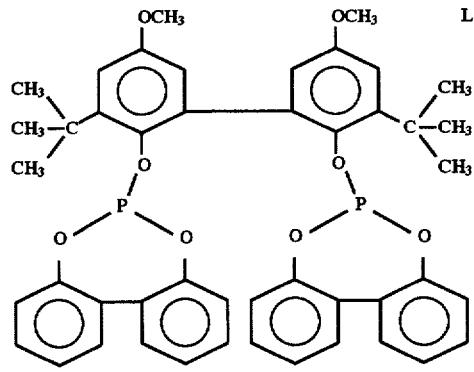

Ligand D 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

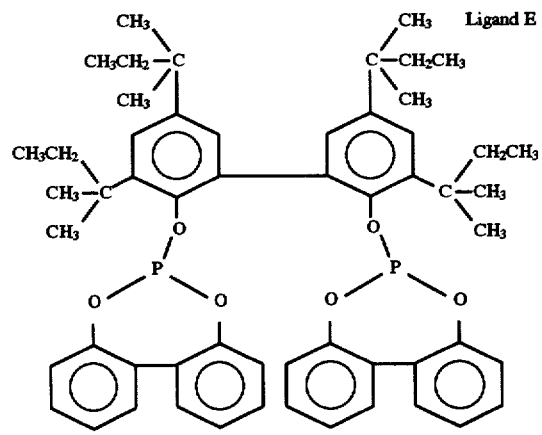

Ligand E 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

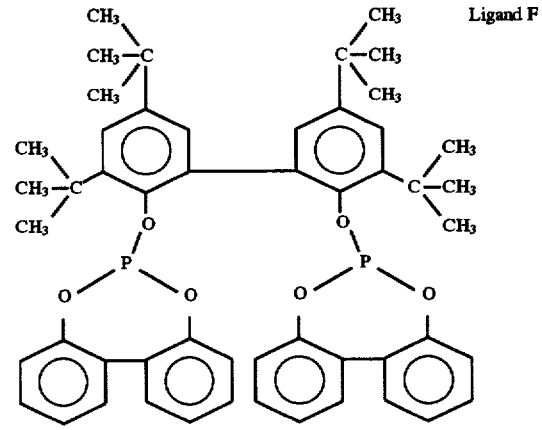

Ligand F (2R,4R)-di[2,2'-(3,3',5,5'-tetrakis-tert-amyl-1,1'-biphenyl)]-2,4-pentyldiphosphite having the formula:
(2R,4R)-di[2,2'-(3,3'-di-tert-butyl-5,5'-dimethyl-1,1'-biphenyl)]-2,4-pentyldiphosphite having the formula:
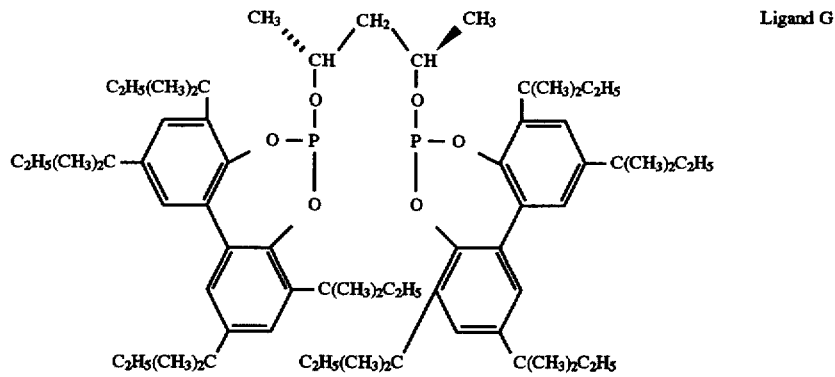
Ligand G
(2R,4R)-di[2,2'-(3,3',5,5'-tetrakis-tert-butyl-1,1'-biphenyl)]-2,4-pentyldiphosphite having the formula:
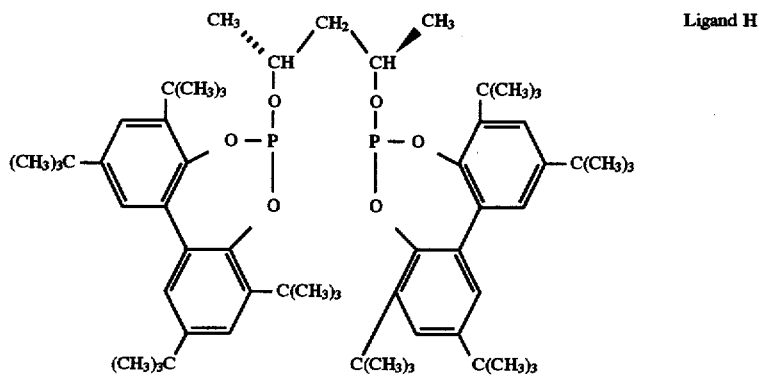
Ligand H
(2R,4R)-di[2,2'-(3,3'-di-amyl-5,5'-dimethoxy-1,1'-biphenyl)]-2,4-pentyldiphosphite having the formula:
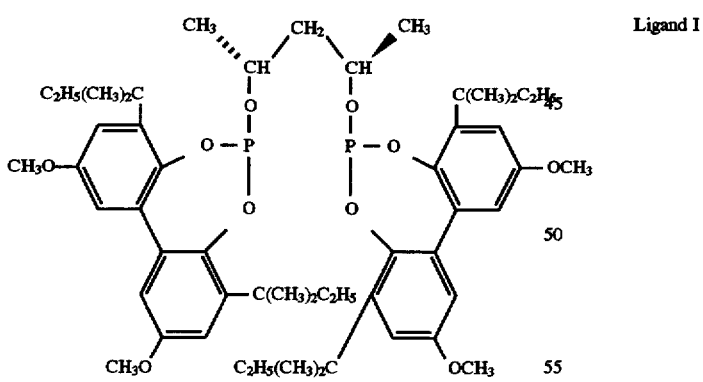
Ligand I

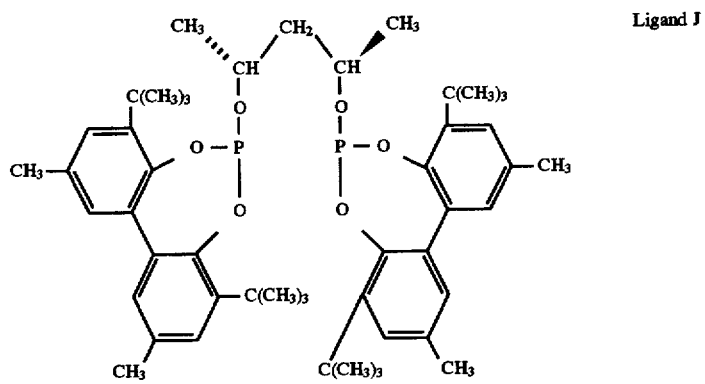
Ligand J
(2R,4R)-di[2,2'-(3,3'-di-tert-butyl-5,5'-diethoxy-1,1'-biphenyl)]-2,4-pentyldiphosphite having the formula:
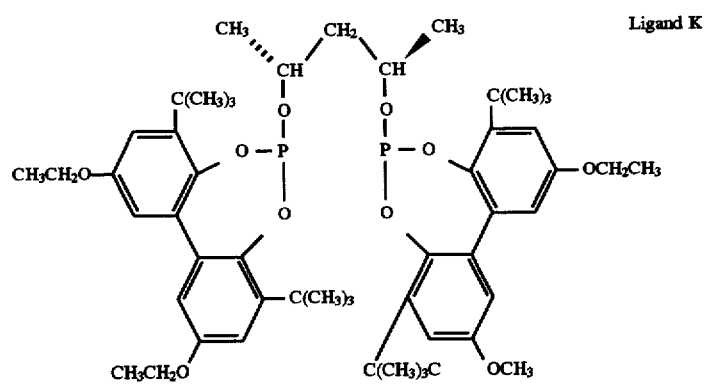
Ligand K
(2R,4R)-di[2,2'-(3,3'-di-tert-butyl-5,5'-diethyl-1,1'-biphenyl)]-2,4-pentyldiphosphite having the formula:
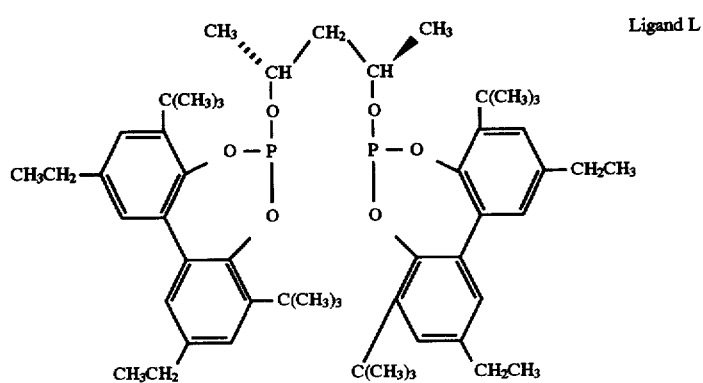
Ligand L
(2R,4R)-di[2,2'-(3,3'-di-tert-butyl-5,5'-dimethoxy-1,1'-biphenyl)]-2,4-pentyldiphosphite having the formula:

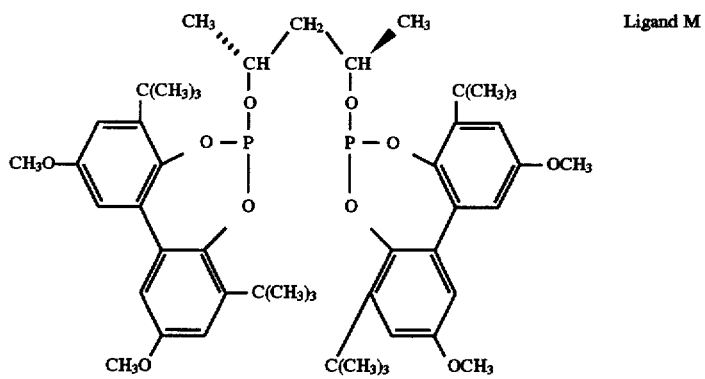

Ligand M

6-[[2'-[(4,6-bis(1,1-dimethylethyl)-1,3,2-benzodioxaphos-phol-2-yl)oxy]-3,3'-bis(1,1-dimethylethyl)-5,5'-dimethoxy-[1,1'-biphenyl]-2-yl]oxy]-4,8-bis(1,1-dimethylethyl)-2,10-dimethoxydibenzo[d,f][1,3,2]dioxaphosphepin having the formula:

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

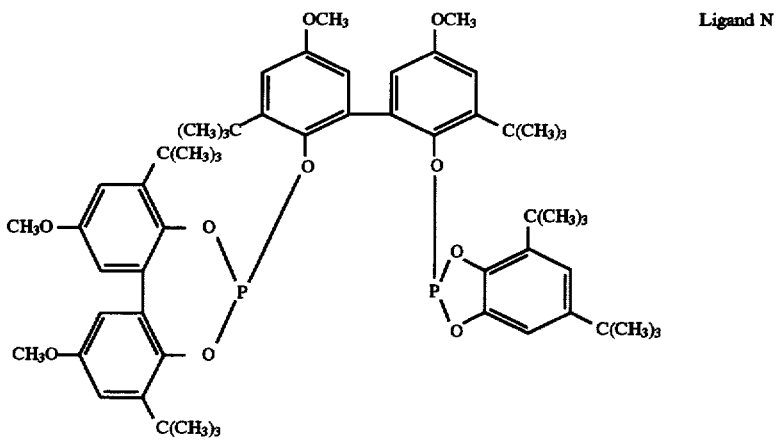

Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

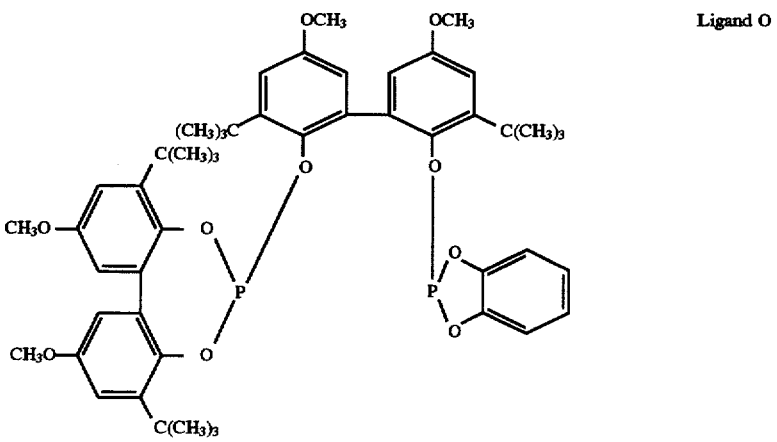

Ligand O

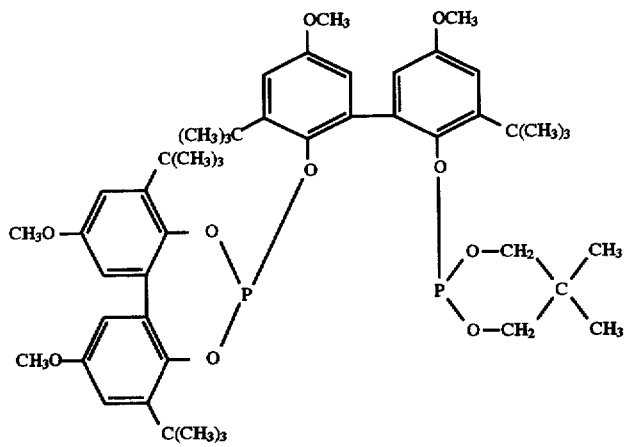

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

3-methoxy-1,3-cyclohexamethylene tetrakis[3,6-bis(1,1-dimethylethyl)-2-naphthalenyl]ester of phosphorous acid having the formula:

Ligand P

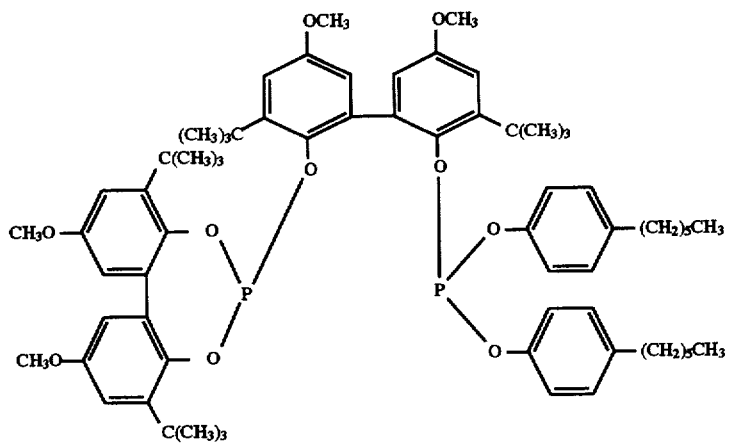

Ligand Q

2-[[2-[[4,8,-bis(1,1-dimethylethyl),2,10-dimethoxydibenzo-[d,f][1,3,2]dioxophosphepin-6-yl]oxy]-3-(1,1-dimethylethyl)-5-methoxyphenyl]methyl]-4-methoxy,6-(1,1-dimethylethyl)phenyl diphenyl ester of phosphorous acid having the formula:

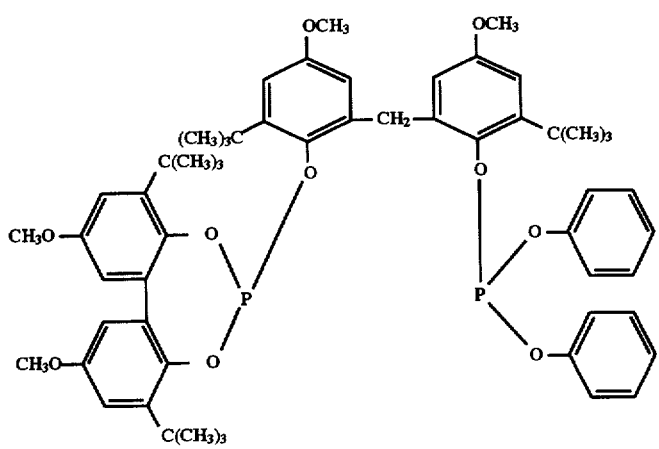

Ligand R 2,5-bis(1,1-dimethylethyl)-1,4-phenylene tetrakis[2,4-bis(1,1-dimethylethyl)phenyl]ester of phosphorous acid having the formula:

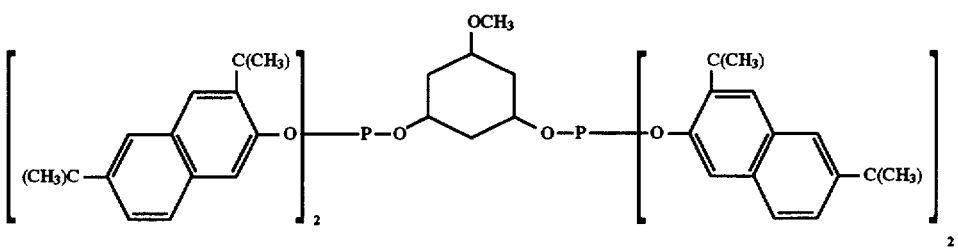

Ligand S methylenedi-2,1-phenylene tetrakis[2,4-bis(1,1-dimethylethyl)phenyl]ester of phosphorous acid having the formula:

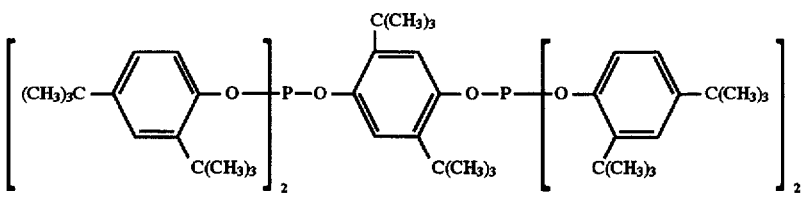

Ligand T

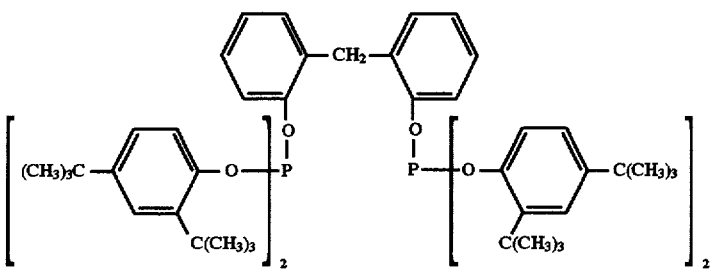

Ligand U

[1,1'-biphenyl]-2,2'-diyl tetrakis[2-(1,1-dimethylethyl)-4-methoxyphenyl]ester of phosphorous acid having the formula:

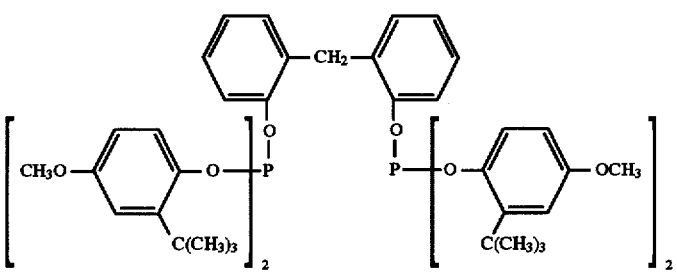

Ligand V

As noted above, the metal-organophosphorus ligand complex catalysts employable in this invention may be formed by methods known in the art. The metal-organophosphorus ligand complex catalysts are preferably in homogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reaction zone along with excess (free) organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-organophosphorus ligand complex precursor catalyst, an organic solvent and free organophosphorus ligand. Such precursor compositions may be prepared by forming a solution of a rhodium starting material, such as a rhodium oxide, hydride, carbonyl or salt, e.g., a nitrate, which may or may not be in complex combination with a organophosphorus ligand as defined herein. Any suitable rhodium starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial rhodium, may be complexed to the rhodium either prior to or in situ during the process.

By way of illustration, the preferred catalyst precursor composition of this invention consists essentially of a solubilized rhodium carbonyl organophosphorus ligand complex precursor catalyst, a solvent and optionally free organophosphorus ligand prepared by forming a solution of rhodium dicarbonyl acetylacetonate, an organic solvent and a organophosphorus ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the processes of this invention. Experience has shown that the acetylacetonate ligand of the precursor catalyst is replaced after the process, e.g., hydroformylation, has begun with a different ligand, e.g., hydrogen, carbon monoxide or organophosphorus ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor rhodium and hydroformylation start-up.

Accordingly, the metal-organophosphorus ligand complex catalysts used in the processes of this invention consists essentially of the metal complexed with carbon monoxide, i.e., hydroformylation, and an organophosphorus ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorus ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The mount of metal-organophosphorus ligand complex catalyst present in the reaction medium of a given process of this invention need only be that minimum mount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 200, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention and preferably the hydroformylation process may be conducted in the presence of an organic solvent for the metal-organophosphorus ligand complex catalyst. The solvent may also contain dissolved water up to the saturation limit. Depending on the particular catalyst and reactants employed, suitable organic solvents include, for example, alcohols, alkanes, alkenes, alkynes, ethers, aldehydes, ketones, esters, amides, mines, aromatics and the like. Any suitable solvent which does not unduly adversely interfere with the intended processes can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that mount sufficient to provide the reaction medium with the particular metal concentration desired for a given process. In general, the mount of solvent when employed may range from about 5 percent by weight up to about 99 percent by weight or more based on the total weight of the reaction mixture starting materials.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The desired products of this invention may be recovered in any conventional manner and one or more separators or separation zones may be employed in any given process to recover the desired reaction product from its crude reaction product fluid. Suitable separation methods include, for example, solvent extraction, crystallization, distillation, vaporization, wiped film evaporation, falling film evaporation and the like. It may be desired to remove the products from the crude reaction mixture as they are formed through the use of trapping agents as described in published Patent Cooperation Treaty Patent Application WO 88/08835. A preferred method for separating the product mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a backmixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

Hydroformylation Processes

A preferred process useful in this invention is hydroformylation. Illustrative metal-organophosphorus ligand complex catalyzed hydroformylation processes which may experience such hydrolytic degradation of the organophosphorus ligand and catalytic deactivation include such processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques of this invention may correspond to any known processing techniques. Preferred process are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organophosphorus ligand complex catalyst in a liquid medium that also contains an organic solvent for the catalyst and ligand. Preferably free organophosphorus ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194 and copending U.S. patent application Ser. No. 08/430,790, filed May 5, 1995, the disclosures of which are incorporated herein by reference, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syn gas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction mixtures employable herein includes any mixture derived from any corresponding hydroformylation process that contains at least some amount of four different main ingredients or components, i.e., the aldehyde product, a metal-organophosphorus ligand complex catalyst, free organophosphorus ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

The substituted or unsubstituted olefin reactants that may be employed in the hydroformylation processes (and other suitable processes) of this invention include both optically active (prochiral and chiral) and non-optically active (achiral) olefinic unsaturated compounds containing from 2 to 40, preferably 2 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more ethylenic unsaturated groups, and of course, mixtures of two or more different olefinic unsaturated compounds may be employed as the staring material if desired. For example, commercial alpha olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, mixed butenes, e.g., Raffinate I and II. Further such olefinic unsaturated compounds and the corresponding products derived therefrom may also contain one or more groups or substituents which do not unduly adversely affect the processes of this invention such as described, for example, in U.S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 2 to 20, carbon atoms, and achiral internal olefins containing from 2 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Illustrative prochiral and chiral olefins useful in the asymmetric hydroformylation processes (and other asymmetric processes) that can be employed to produce enantiomeric product mixtures that may be encompassed by in this invention include those represented by the formula:

 (XII)

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation processes (and other asymmetric processes) of this invention include, for example, p-isobutylstyrene, 2-vinyl-6-methoxy-2- naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-organophosphorus ligand complex catalyst as described hereinabove. The metal-organophosphorus ligand complex catalyst does not undergo substantial deactivation in the presence of solely carbon monoxide and hydrogen and/or effects a change in normal aldehyde selectivity of less than 0.2 percent of normal aldehyde per 1 pound per square inch of carbon monoxide partial pressure. The hydroformylation catalysts may be in homogeneous form during the reaction and/or during the product separation. Of course mixtures of such catalysts can also be employed if desired. The amount of metal-organophosphorus ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 400 parts per million of metal, e.g., rhodium.

In addition to the metal-organophosphorus ligand complex catalyst, free organophosphorus ligand (i.e., ligand that is not complexed with the metal) may also be present in the hydroformylation reaction medium. The free organophosphorus ligand may correspond to any of the above-defined organophosphorus ligands employable herein. It is preferred that the free organophosphorus ligand be the same as the organophosphorus ligand of the metal-organophosphorus ligand complex catalyst employed. However, such ligands need not be the same in any given process. The hydroformylation process of this invention may involve from about 0.1 moles or less to about 400 moles or higher, of free organophosphorus ligand per mole of metal in the hydroformylation reaction medium. Preferably the hydroformylation process of this invention is carried out in the presence of from about 1 to about 200 moles of organophosphorus ligand, and more preferably for organopolyphosphites from about 1.1 to about 4 moles of organopolyphosphite ligand, per mole of metal present in the reaction medium; said amounts of organophosphorus ligand being the sum of both the amount of organophosphorus ligand that is bound (complexed) to the metal present and the amount of free (non-complexed) organophosphorus ligand present. Since it is more preferred to produce non-optically active aldehydes by hydroformylating achiral olefins, the more preferred organophosphorus ligands are achiral type organophosphorus ligands, especially those encompassed by Formula (I) above, and more preferably those of Formulas (II) and (V) above. Of course, if desired, make-up or additional organophosphorus ligand can be supplied to the reaction medium of the hydroformylation process at any time and in any suitable manner, e.g. to maintain a predetermined level of free ligand in the reaction medium.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 500 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about $-25°$ C. to about $200°$ C. In general hydroformylation reaction temperatures of about $50°$ C. to about $120°$ C. are preferred for all types of olefinic starting materials. Of course it is to be understood that when non-optically active aldehyde products are desired, achiral type olefin starting materials and organophosphorus ligands are employed and when optically active aldehyde products are desired prochiral or chiral type olefin starting materials and organophosphorus ligands are employed. Of course, it is to be also understood that the hydroformylation reaction conditions employed will be governed by the type of aldehyde product desired.

The hydroformylation processes encompassed by this invention are also conducted in the presence of an organic solvent for the metal-organophosphorus ligand complex catalyst and free organophosphorus ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 3 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorus ligand complex catalyst, and free organophosphorus ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-organophosphorus complex catalyst mixture separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, phase separation, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction mixture, removed from the reaction zone can be passed to a separation zone, e.g., vaporizer/separator, wherein the desired aldehyde product can be separated via distillation, in one or more stages, under normal, reduced or elevated pressure, from the liquid reaction mixture, condensed and collected in a product receiver, and further purified if desired. The remaining non-volatilized catalyst containing liquid reaction mixture may then be recycled back to the reaction zone as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product from the metal-organophosphorus complex catalyst containing reaction mixture may take place at any suitable temperature desired. In general, it is recommended that such distillation take place at relatively low temperatures, such as below 150° C., and more preferably at a temperature in the range of from about 50° C. to about 140° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reaction zone to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

EXAMPLE 1

A single reactor vessel with three reactive stages was used to hydroformylate ethylene to propionaldehyde. The vessel was divided into three stages by physical horizontal barriers. Reactants were all fed to the bottom reactive stage and progressed vertically upward through the vessel. The bottom portion of the vessel accounted for 43% of the volume available for hydroformylation. The middle portion of the vessel accounted for 28% of the volume, and the top portion of the reactor was the remaining volume available for reaction. The vessel was equipped with an agitator mounted at the top of the vessel providing agitation within each individual reactive stage. The catalyst used in the hydroformylation consisted of 107 parts per million rhodium as rhodium metal, 3.8 weight percent triphenylphosphine, and 31.5 weight percent propionaldehyde condensation products, with the balance of the catalyst consisting of propionaldehyde, unconverted reactants, and other hydroformylation byproducts such as ethane. The feed rates of the reactants to the reactor vessel expressed as standard cubic feet per hour per cubic foot of total hydroformylation volume of ethylene, hydrogen, and carbon monoxide, was 97.8 ft3 ethylene/ft3 hydroformylation volume/hr, 106.2 ft3 hydrogen/ft3 hydroformylation volume/hr, and 102.8 ft3 carbon monoxide/ft3 hydroformylation volume/hr respectively. Inerts amounting to 3.8 ft3/ft3 hydroformylation volume/hr were also fed to the reactor with the feeds (standard conditions for this example are 32° F., and 1 atmosphere). The hydroformylation was carried out at a temperature of 88° C. in the bottom compartment, 86° C. in the middle compartment, and 83° C. in the top compartment. Total pressure of the reaction vessel was 275 psia. The resulting partial pressures in the vapor vent from the top of the reactor for the ethylene, hydrogen, and carbon monoxide were 1.5 psi, 127 psi, and 77 psi respectively. The overall reaction rate to propionaldehyde achieved was 4.2 gmol/L/hr. The product was separated from the catalyst and the concentrated catalyst was recycled to the baffled reactor vessel.

EXAMPLE 2

A hydroformylation system with 350 parts per million by weight rhodium metal, 20 weight percent triphenylphosphine, 50 weight percent butyraldehyde, and the balance of the solution being aldehyde condensation byproducts, other reaction byproducts or reactants, gives the percent changes in hydroformylation rate with respect to carbon monoxide partial pressure as set forth in Table A below. The partial pressures of the other reactants are 100 psi propylene, 50 psi hydrogen, and the value for the partial pressure of carbon monoxide is given in Table A. Temperature of the reaction is 110° C. Pressure of the reaction is at least the total of the partial pressures of the reactants.

TABLE A

| Partial Pressure of CO, psi | Percent change in Hydroformylation Reaction Rate |
| --- | --- |
| 3.5 | 13.6 |
| 5.5 | 8.1 |
| 7.5 | 5.4 |
| 9.5 | 3.8 |
| 29.5 | 0.4 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing one or more products in a multistaged reactor which process comprises reacting in said multistaged reactor one or more reactants with carbon monoxide in the presence of a metal-organophosphorus ligand complex catalyst and optionally free organophosphorus ligand to produce said one or more products, wherein said metal-organophosphorus ligand complex catalyst does not undergo substantial deactivation in the presence of solely carbon monoxide and/or effects a change in normal product selectivity of less than 0.2 percent of normal product per 1 pound per square inch of carbon monoxide partial pressure.

2. A hydroformylation process for producing one or more aldehydes in a multistaged reactor which process comprises reacting in said multistaged reactor one or more olefinic unsaturated compounds with carbon monoxide and hydrogen in the presence of a metal-organophosphorus ligand complex catalyst and optionally free organophosphorus ligand to produce said one or more aldehydes, wherein said metal-organophosphorus ligand complex catalyst does not undergo substantial deactivation in the presence of solely carbon monoxide and hydrogen and/or effects a change in normal aldehyde selectivity of less than 0.2 percent of normal aldehyde per 1 pound per square inch of carbon monoxide partial pressure.

3. A process for producing one or more products in a multistaged reactor which process comprises reacting in said multistaged reactor one or more reactants with carbon monoxide in the presence of a metal-organophosphorus ligand complex catalyst and optionally free organophosphorus ligand to produce said one or more products, wherein said metal-organophosphorus ligand complex catalyst does not undergo substantial deactivation in the presence of solely carbon monoxide and/or effects a change in normal product selectivity of less than 0.2 percent of normal product per 1 pound per square inch of carbon monoxide partial pressure and/or effects a change in reaction rate of less than 2 percent per 1 pound per square inch of carbon monoxide partial pressure.

4. A hydroformylation process for producing one or more aldehydes in a multistaged reactor which process comprises reacting in said multistaged reactor one or more olefinic unsaturated compounds with carbon monoxide and hydrogen in the presence of a metal-organophosphorus ligand complex catalyst and optionally free organophosphorus ligand to produce said one or more aldehydes, wherein said metal-organophosphorus ligand complex catalyst does not undergo substantial deactivation in the presence of solely carbon monoxide and hydrogen and/or effects a change in normal aldehyde selectivity of less than 0.2 percent of normal aldehyde per 1 pound per square inch of carbon monoxide partial pressure and/or effects a change in reaction rate of less than 2 percent per 1 pound per square inch of carbon monoxide partial pressure.

5. The process of claim 1 in which the staged reactor comprises: a substantially vertically-oriented reactor means; a stirring means inside said reactor means, said stirring means being operatively associated with said reactor means and comprising an elongated rod means having a plurality of blades disposed about said rod means, said stirring means extending substantially throughout the entire length of said reactor means; at least two reactants entrance means in the lower portion of said reactor means for continuously conveying one or more olefinic compounds, one or more metal-organophosphorus ligand complex catalysts and a source of hydrogen and carbon monoxide into said reactor means; optionally at least one reactants entrance means in the upper portion of said reactor means for continuously conveying one or more olefinic compounds, one or more metal-organophosphorus ligand complex catalysts and/or a source of hydrogen and carbon monoxide into said reactor means; at least one product exit means in the upper portion of said reactor means for continuously removing product, metal-organophosphorus ligand complex catalyst and unreacted reactants from said reactor means; and at least one baffle means on the inside surface of said reactor means, said baffle means being spaced in such a manner that said baffle means are interspaced in-between said blades of said stirring means.

6. The process of claim 5 in which the staged reactor further comprises a heat removal means comprising external loop and/or internal coils.

7. The process of claim 1 in which the staged reactor comprises: a substantially vertically-oriented vessel; a plurality of generally horizontal baffles disposed within said vessel and dividing the interior of said vessel into a plurality of chambers, each said baffle being formed with a central hole and being mounted on the inner wall of said vessel; at least two inlet means for feeding one or more olefinic compounds, one or more metal-organophosphorus ligand complex catalysts and a source of hydrogen and carbon monoxide into one or more lower chambers; optionally at least one inlet means for feeding one or more olefinic compounds, one or more metal-organophosphorus ligand complex catalysts and/or a source of hydrogen and carbon monoxide into one or more upper chambers; at least one outlet means for removing hydroformylation products, metal-organophosphorus ligand complex catalysts and unreacted reactants from one or more upper chambers; a rotatable generally vertical drive shaft centrally positioned to rotate in said vessel and extending generally concentrically through each said hole in each said baffle; and a plurality of impellers each mounted for rotation on said shaft and generally positioned above or below each said hole of said horizontal baffles, said impellers being of a size relative to said holes to sufficiently provide mixing of said hydroformylation reactants, metal-organophosphorus ligand complex catalysts and products as they move from a lower chamber upward to an adjacent chamber whereby said hydroformylation reactants, metal-organophosphorus ligand complex catalysts and products are caused to be well mixed within each chamber.

8. The process of claim 7 in which the staged reactor further comprises a heat removal means comprising external loop and/or internal coils.

9. The process of claim 1 in which the staged reactor comprises: a vertical cylindrical vessel with a plurality of spaced stationary horizontal imperforate baffles dividing said vessel into superposed compartments, said baffles having central apertures therein for communication between said compartments; an upstanding flange disposed around the circumference of the central aperture of each compartment; a shaft rotatably mounted axially of said vessel and extending through said compartments and an agitating means for the shaft; a means for admitting carbon monoxide, hydrogen, one or more metal-organophosphorus ligand complex catalysts and one or more olefinic compounds into the lower-most compartment; and a means for withdrawing product aldehyde, metal-organophosphorus ligand complex catalyst and unreacted reactants from the upper-most compartment.

10. The process of claim 1 in which the staged reactor comprises: a vessel with an elongated generally cylindrical chamber therein; an agitator shaft extending coaxially through the chamber, the shaft extending outside the chamber and being provided with means for driving the same; a plurality of transverse partitions in the chamber open at their centers around the agitating shaft dividing the chamber into a lineal series of compartments in open communication with one another; an agitator for providing essentially complete backmixing in each compartment; vertical baffles in each compartment projecting radially toward the center to prevent swirling of fluids being agitated, designed to produce in each compartment upon rotation of the agitator a cyclical flow of fluid and gas from the periphery of the agitator to the peripheral wall of the chamber, thence lengthwise of the chamber in each direction along the walls of the compartment, and thence radially inwardly adjacent said partitions toward the shaft; a means for admitting carbon monoxide, hydrogen, one or more metal-organophosphorus ligand complex catalysts and one or more olefinic compounds into the lower-most compartment; and a means of withdrawing product aldehyde, metal-organophosphorus ligand complex catalyst and unconverted reactants from the upper-most compartment.

11. The process of claim 1 in which the reactive stages are physically separated by baffle plates with passages from reactive stage to reactive stage where said passages are such that gas and liquid backflow is minimized.

12. The process of claim 1 in which the reactive stages are separated by designed mixing patterns which create regions of varying concentrations and allow for gas and liquid flow from reactive stage to reactive stage.

13. The process of claim 1 which comprises a hydroformylation, hydroacylation (intramolecular and intermolecular), hydroamidation, hydroesterification or carbonylation process.

14. The process of claim 1 wherein said metal-organophosphorus ligand complex catalyst comprises rhodium complexed with an organophosphorus ligand having the formula selected from:

(i) a triorganophosphine ligand represented by the formula:

wherein $R^1$ is the same or different and represents a substituted or unsubstituted monovalent hydrocarbon radical containing from 1 to 24 carbon atoms or greater;

(ii) a monoorganophosphite represented by the formula:

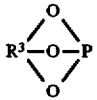

wherein $R^3$ represents a substituted or unsubstituted trivalent hydrocarbon radical containing from 4 to 40 carbon atoms or greater;

(iii) a diorganophosphite represented by the formula:

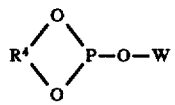

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and represents a substituted or unsubstituted monovalent hydrocarbon radical; and (v) an organopolyphosphite containing two or more tertiary (trivalent) phosphorus atoms represented by the formula:

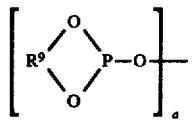

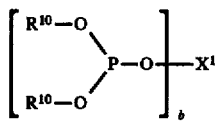

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

* * * * *